United States Patent [19]

Sugi

[11] Patent Number: 4,968,666

[45] Date of Patent: Nov. 6, 1990

[54] CLATHRATE COMPOUND

[75] Inventor: Hideo Sugi, Tokyo, Japan

[73] Assignee: Kurita Water Industries Ltd., Tokyo, Japan

[21] Appl. No.: 302,848

[22] Filed: Jan. 26, 1989

[30] Foreign Application Priority Data

Feb. 18, 1988 [JP] Japan .................................. 63-36363

[51] Int. Cl.$^5$ ................................................ A61K 7/46
[52] U.S. Cl. ......................................... 512/4; 424/405
[58] Field of Search ............................. 512/4; 424/405

[56] References Cited

U.S. PATENT DOCUMENTS 4,725,633  2/1988  Shibanai .............................. 523/220

OTHER PUBLICATIONS

Merck Index, 10th Ed, #65, p. 70 (1983).
Meirovitch, J. Phys. Chem 89, 2385 (1985).
Chan; Tai-Wan Yao Hsueh Thu Chi, 3Y, 23 (1982).

*Primary Examiner*—Robert Gerstl
*Attorney, Agent, or Firm*—Kanesaka and Takeuchi

[57] ABSTRACT

A clathrate compound comprises a natural essential oil or synthetic perfume, and deoxycholic acid. Deoxycholic acid or a solution containing deoxycholic acid is mixed with a natural essential oil or synthetic perfume to produce the clathrate compound.

2 Claims, No Drawings

CLATHRATE COMPOUND

Field of the Invention and Related Art Statement:

This invention relates to a clathrate compound and a method of producing a clathrate compound. More particularly, it relates to a clathrate compound which provides a novel sustained release aromatic or microbicide maintaining its aromatic or microbicidal or insecticidal effect for a long period of time and having an improved degree of stability, and a method of producing any such clathrate compound.

The aromatics which are used in living rooms, hotel rooms and lobbies, automobiles, toilet rooms, etc. are classified into three types, i.e. solid, liquid and aerosol.

A solid aromatic is a product molded from a mixture of a perfume, a plasticizer, a stabilizer and a porous powdery material. It is usually so designed as to be capable to use for an ornamental role, too, in the place where it is used.

A container for holding a liquid aromatic is provided at its opening with a volatalizing material, such as felt or filter paper, by which the aromatic is drawn up to release a pleasant smell by volatilization. The volatilizing material and the opening of the container are so controlled as to vary the rate at which the aromatic volatilizes.

An aerosol type aromatic can always produce a pleasant smell instantaneously and effectively when it is sprayed into the air. Two kinds of dispersing agents, i.e. freons (chlorofluorocarbons) and alcohols, and LPG and water (with a surface active agent), are used for preparing aerosols.

The solid aromatic has the drawback that the application of heat during its molding step makes it difficult to employ a perfume having a low boiling point. The liquid aromatic has the drawback of spilling if its container falls.

The aerosol type aromatic has the drawback of being applicable to only a limited range of perfumes. It is necessary to avoid use of any perfume that is likely to undergo any chemical change or corrode in a can in which it is held, as use of any such perfume might result in an undesirable change of smell which is released, or formation of an unstable emulsion leading to clogging of a valve through which the aerosol is discharged.

Similar problems have been found to exist in the conventional microbicides, too.

Objects and Summary of the Invention:

It is an object of this invention to provide a clathrate compound giving an excellent sustained release antimicrobial agent, insecticide or aromatic which can overcome the drawbacks of the prior art as hereinabove pointed out, and a method of producing any such clathrate compound.

It is another object of this invention to provide a clathrate compound which is easy to mold into a particular shape, use and handle, and a method of producing any such clathrate compound.

The clathrate compound of this invention comprises a natural essential oil or synthetic perfume, and deoxycholic acid.

The method of this invention comprises mixing deoxycholic acid or a solution containing deoxycholic acid with a natural essential oil or synthetic perfume. Detailed Description of Preferred Embodiments:

Referring in detail to the clathrate compound of this invention, it is a compound formed by molecular imprisonment of a natural essential oil or synthetic perfume as a guest compound in deoxycholic acid as a host compound.

A natural essential oil of synthetic perfume is used as the guest compound forming the clathrate compound of this invention. Examples of the essential oils which can be used are cineole, hinoki oil, cinnamon oil, quassia oil, menthol, rose oil, rosemary oil, palmarosa oil, lavender oil, spearmint oil, and mentha arvensis. Examples of the synthetic perfumes which can be used are fragrant olive (Osmanhus), jasmine oil and lemon oil. The essential oils have an insecticidal or microbicidal action, too. It is also possible to use a mixture of two or more quest compounds. Deoxycholic acid is used as the host compound forming the clathrate compound of this invention. It is a natural substance which is represented by the following formula, and is commercially available:

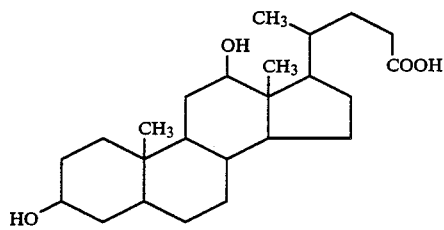

The clathrate compound of this invention can be produced easily either by employing a solvent, a dispersant, or not. When a solvent or a dispersant is employed, the host compound is dissolved or dispersed in a customary solvent or dispersant, such as methanol, ethanol, acetone, benzene or chloroform, and a liquefied natural essential oil or synthetic perfume is added to the solution or dispersion of the most compound, so that they may react with each other. Then, the solvent or dispersant is removed by evaporation from the reaction mixture, or it is left a standstill for some time, whereupon a solid clathrate compound is precipitated. It is collected by a customary method of filtration.

When no solvent is employed, deoxycholic acid is directly added to a liquefied or liquid essential oil or synthetic perfume, so that- they may react with each other. Thereafter, the precipitate is separated by the same way mentioned above The clathrate compound can be easily produced by either the method employing a solvent or the method not employing any solvent. According to this invention, however, it is preferable not to employ any solvent, as if a solvent is employed, a number of problems, including the following, is likely to occur:

(1) It is necessary to choose an appropriate solvent;
(2) It is relatively difficult to establish appropriate conditions;
(3) Separation of a solid product from liquid leaves waste matter which required special disposal;
(4) It is necessary to provide facilities for protecting workers and their working environment, especially if an organic solvent is used; and
(5) The host compound can be recovered only at a relatively low rate.

The method of this invention does not necessarily require the guest compound to consist solely of a natural essential oil or synthetic perfume, but permits the use of a mixture containing impurities. As deoxycholic acid undergoes a very selective reaction with the guest compound, it is possible to produce a clathrate compound containing only the desired guest compound, even if the starting material may contain impurities.

A reaction temperature of 0°C. to 100°C. is employed for producing a clathrate compound by the method of this invention, whether a solvent may be used, or not. A range of, say, 10° C to 50° C is preferred. It is sufficient to continue the reaction for a period of, say, 0.1 to 24 hours. The host and guest compounds are employed in the proportions which are, say, 1 to 3 times as large as their reaction equivalents.

The clathrate compound which can be produced in accordance with this invention is a compound formed by the selective inclusion of the guest compound in the host compound. This fact can be ascertained by the NMR spectrum of the clathrate compound. The NMR analysis of the clathrate compound also reveals the molar ratio of the guest compound which it contains.

The clathrate compound of this invention is usually a powdery solid and can, therefore, be used for a wide variety of purposes if its particle size is varied, or if it is molded into various shapes.

The clathrate compound of this invention can be used in a variety of ways including the following:
(1) The compound is placed in a container having an opening;
(2) It is molded into an appropriate shape;
(3) A mixture of the compound with a paint or any other resinous coating material is applied onto the surface of an object;
(4) The compound is caused by an appropriate method to adhere to the surface of an object; and
(5) A mixture of the compound [with ink, particularly an aqueous ink (or medium alone), is applied by printing onto the surface of an object.

The clathrate compound of this invention is useful as an aromatic, whether the guest compound may be an essential oil or a synthetic perfume. If the guest compound is an essential oil, it has an insecticidal or antimicrobial action, too.

More specifically, the clathrate compound of this invention can be used for making, for example:
(1) Aromatic or insecticidal ornamental articles for use in a room or automobile;
(2) Aromatic or insecticidal building or flooring materials;
(3) Aromatic or insecticidal furniture;
(4) Aromatic or insecticidal bedding articles;
(5) Toiletry (cosmetics, preparations for use in bathing or washing, etc.);
(6) Aromatic toys;
(7) Aromatic personal outfitting
(8) Aromatic accessories;
(9) Aromatic stationery; and
(10) Aromatic articles for sanitary use.

The clathrate compound of this invention releases an essential oil or synthetic perfume slowly, as it is imprisoned in deoxycholic acid. Therefore, it provides an excellent sustained release aromatic or insecticidal or microbicidal agent which can maintain its aromatic or insecticidal or microbicidal effect for a long period of time. The rate at which the essential oil or synthetic perfume volatilizes is easy to control if the particle size of the clathrate compound is varied, or if it is molded into a different shape.

The clathrate compound of this invention can be molded into any desired shape at ordinary room temperature. Therefore, it can contain any perfume having even a low boiling point without causing it to change its nature when the compound is molded into a particular shape.

The invention will now be described in further detail with reference to several examples thereof.

Example 1:

A mixture of 1.3 g of deoxycholic acid and 0.9 g of cineole was fully stirred at room temperature. Their reaction proceeded rapidly and yielded a white solid product. The examination of the product through an electron microscope confirmed that it was a crystalline substance. The NMR analysis of the product revealed that it contained 40% by weight of cineole.

Example 2:

Two grams of cineole were added to the solution which had been obtained by dissolving 1.3 g of deoxycholic acid in 5 ml of methanol. They were allowed to react with each other at room temperature for 24 hours under stirring, whereby a solid reaction product was obtained. It was collected by filtration, and was dried. The NMR analysis of the product revealed that it contained 26% by weight of cineole.

Example 3

A producing a variety of
Example 1 was repeated for producing a variety of clathrate compounds by employing hinoki oil, quassia oil, rose oil, lemon oil, rosemary oil mentha arvensis, or lavender oil as the guest compounds. The NMR analysis of the products revealed that they contained 40, 26, 31, 30, 41, 40, or 43% by weight of the guest compounds, respectively.

Example 4:

A sustained release test was conducted on each of the clathrate compounds which had been produced by employing cineole and hinoki oil in Examples 1 and 3, respectively. One to one and a half grams of each compound were placed in a laboratory dish. The dish was left in an open place at a temperature of 25°C. and a reduction in weight of the compound was examined from time to time. The results are shown in Table 1.

TABLE 1

| Total reduction | Days elapsed | | | | | |
|---|---|---|---|---|---|---|
| (wt. %) | 2 | 4 | 6 | 8 | 21 | 40 |
| Cineole | 50.1 | 54.7 | 55.8 | 57.0 | 60.0 | 63.8 |
| Hinoki oil | 44.2 | 50.0 | 55.0 | 57.1 | 59.4 | 59.6 |

As is obvious from Table 1, the clathrate compounds of this invention released the guest compounds only very slowly, or exhibited an excellent sustained release property.

What is claimed is:
1. A clathrate compound comprising:
a deoxycholic acid; and
a guest compound selected from the group consisting of a natural essential oil, a synthetic perfume and the mixture thereof, said essential oil being selected from the group consisting of cineole, hinoki oil, cinnamon oil, quassia oil, menthol, rose oil, rosemary oil, palmarosa oil, lavender oil, spearmint oil and mentha arvensis.
2. A clathrate compound comprising:
deoxycholic acid; and
a guest compound selected from the group consisting of a natural essential oil, a synthetic perfume and the mixture thereof, said perfume being selected from the group consisting of Japanese olive oil, jasmine oil and lemon oil.

* * * * *